(12) United States Patent
Annest et al.

(10) Patent No.: US 8,123,668 B2
(45) Date of Patent: Feb. 28, 2012

(54) SIGNAL TRANSMITTING AND LESION EXCLUDING HEART IMPLANTS FOR PACING DEFIBRILLATING AND/OR SENSING OF HEART BEAT

(75) Inventors: Lon S. Annest, Tacoma, WA (US); Arthur A. Bertolero, Danville, CA (US); David K. Swanson, Campbell, CA (US)

(73) Assignee: BioVentrix (A CHF Technologies' Company), San Ramon, CA (US)

( * ) Notice: Subject to any disclaimer, the term of this patent is extended or adjusted under 35 U.S.C. 154(b) by 975 days.

(21) Appl. No.: 11/536,553

(22) Filed: Sep. 28, 2006

(65) Prior Publication Data

US 2008/0082132 A1 Apr. 3, 2008

(51) Int. Cl.
*A61N 1/362* (2006.01)
(52) U.S. Cl. .............. 600/16; 600/17; 607/4; 607/5; 607/9
(58) Field of Classification Search .............. 600/16–18; 607/2, 4, 5, 6, 9
See application file for complete search history.

(56) References Cited

U.S. PATENT DOCUMENTS

| | | | |
|---|---|---|---|
| 6,059,715 A | 5/2000 | Schweich, Jr. et al. | |
| 6,125,852 A | 10/2000 | Stevens et al. | |
| 6,162,168 A | 12/2000 | Schweich, Jr. et al. | |
| 6,258,021 B1* | 7/2001 | Wilk | 600/16 |
| 6,572,529 B2* | 6/2003 | Wilk | 600/16 |
| 6,616,684 B1 | 9/2003 | Vidlund et al. | |
| 6,709,382 B1* | 3/2004 | Horner | 600/16 |
| 6,776,754 B1 | 8/2004 | Wilk | |
| 6,808,488 B2 | 10/2004 | Mortier | |
| 2002/0120298 A1* | 8/2002 | Kramer et al. | 607/5 |
| 2002/0123768 A1* | 9/2002 | Gilkerson et al. | 607/5 |
| 2003/0163165 A1* | 8/2003 | Bornzin et al. | 607/5 |
| 2003/0181951 A1* | 9/2003 | Cates | 607/9 |
| 2005/0288613 A1* | 12/2005 | Heil | 602/16 |

* cited by examiner

*Primary Examiner* — Carl H Layno
*Assistant Examiner* — Allen Porter, Jr.
(74) *Attorney, Agent, or Firm* — Kilpatrick Townsend & Stockton LLP

(57) ABSTRACT

Devices, systems, and methods for treating a heart of a patient may make use of structures which limit a size of a chamber of the heart, such as by deploying a tensile member to bring a wall of the heart toward (optionally into contact with) a septum of the heart. The implant may include an electrode or other structure for applying pacing signals to one or both ventricles of the heart, for defibrillating the heart, for sensing beating of the heart or the like. A wireless telemetry and control system may allowing the implant to treat congestive heart failure, monitor the results of the treatment, and apply appropriate electrical stimulation.

16 Claims, 12 Drawing Sheets

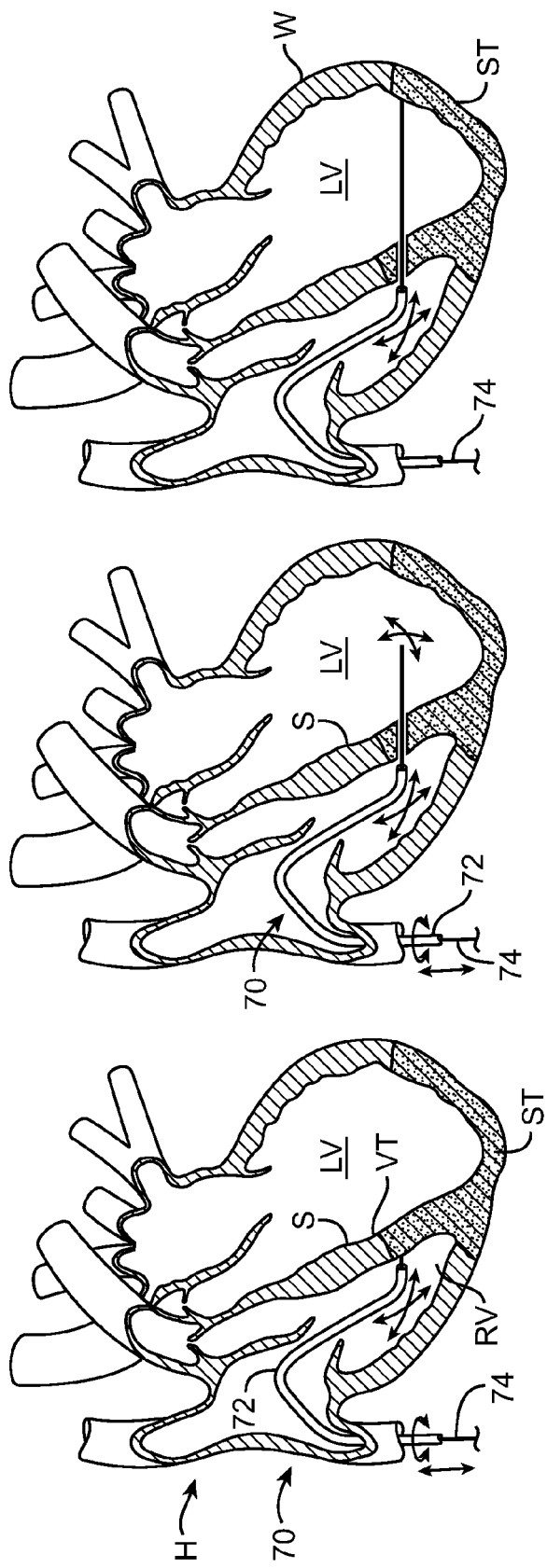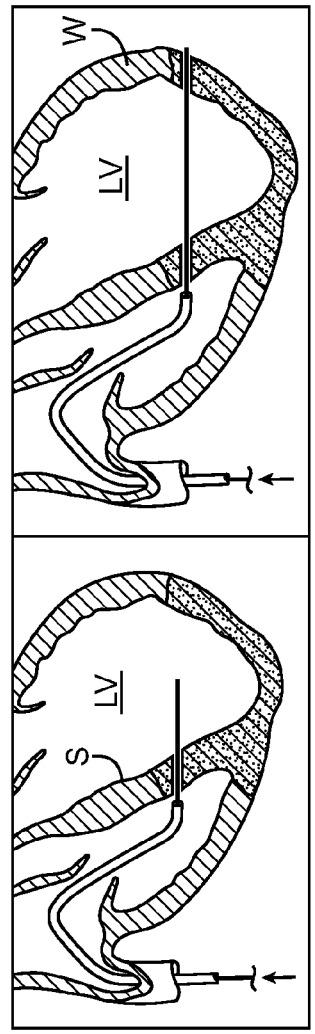

SIGNAL TRANSMITTING AND LESION EXCLUDING HEART IMPLANTS FOR PACING DEFIBRILLATING AND/OR SENSING OF HEART BEAT

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The present invention is generally directed to improved devices, systems, and methods for treatment of the heart. Exemplary embodiments provide implants and methods for alleviating congestive heart failure and other progressive diseases, for pacing (often biventricular pacing), for monitoring beating of the heart, and/or the like. Congestive heart failure may, for example, be treated using an implant which excludes scar tissue and limits a cross section across a ventricle, with the implant also being used to help in sensing the heart function and pacing or (as needed) defibrillating the heart.

Congestive heart failure (sometimes referred to as "CHF" or "heart failure") is a condition in which the heart does not pump enough blood to the body's other organs. Congestive heart failure may in some cases result from narrowing of the arteries that supply blood to the heart muscle, high blood pressure, heart valve dysfunctions due to rheumatic fever or other causes, cardiomyopathy (a primary disease of the heart muscle itself), congenital heart defects, infections of the heart tissues, and the like. However, in most cases congestive heart failure may be triggered by a heart attack or myocardial infarction. Heart attacks can cause scar tissue that interferes with the heart muscle's healthy function, and that scar tissue can progressively replace more and more of the heart tissue. More specifically, the presence of the scar may lead to a compensatory neuro-hormonal response by the remaining, non-infarcted myocardium.

People with heart failure may have difficulty exerting themselves, often becoming short of breath, tired, and the like. As blood flow out of the heart slows, blood returning to the heart through the vascular system decreases, causing congestion in the tissues. Edema or swelling may occur in the legs and ankles, as well as other parts of the body. Fluid may also collect in the lungs, interfering with breathing (especially when lying down). Congestive heart failure may also decrease the ability of the kidneys to remove sodium and water, and the fluid buildup may be sufficient to cause substantial weight gain. With progression of the disease, this destructive sequence of events can cause the eventual failure of the remaining functional heart muscle.

Treatments for congestive heart failure may involve rest, dietary changes, and modified daily activities. Various drugs may also be used to alleviate detrimental effects of congestive heart failure, such as by expanding blood vessels, improving and/or increasing pumping of the remaining healthy heart tissue, increasing the elimination of waste fluids, and the like.

Surgical interventions have also been applied for treatment of congestive heart failure. If the heart failure is related to an abnormal heart valve, the valve may be surgically replaced or repaired. Techniques also exist for exclusion of the scar and volume reduction of the ventricle. These techniques may be involve (for example) surgical left ventricular reconstruction, ventricular restoration, the Dor procedure, and the like. If the heart becomes sufficiently damaged, even more radical surgery may be considered. For example, a heart transplant or a ventricular assist device may be the most viable options for some patients. These surgical therapies can be at least partially effective, but typically involve substantial patient trauma. While people with mild or moderate congestive heart failure may benefit from these known techniques to alleviate the symptoms and/or slow the progression of the disease, less traumatic therapies which significantly increase the heart function and extend life of congestive heart failure patients has remained a goal.

It has recently been proposed that a device be applied to or implant be placed in the heart of certain patients with congestive heart failure so as to reduce ventricular volume. With congestive heart failure, the left ventricle often dilates or increases in size. This can result in a significant increase in wall tension and stress. With disease progression, the volume of the left ventricle gradually increases while forward blood flow gradually decreases, with scar tissue often taking up a greater and greater percentage of the ventricle wall. By implanting a device which brings opposed walls of the ventricle into contact with one another, a portion of the ventricle may be constricted or closed off, thereby reducing volume. By reducing the overall size of the ventricle, particularly by reducing the portion of the functioning ventricle chamber formed by scar tissue, the heart function may be significantly increased and the effects of disease progression may be at least temporarily reversed, halted, and/or slowed.

An exemplary method and implant for closing off a lower portion of a heart ventricle is shown in FIG. 1, and is more fully described in U.S. Pat. No. 6,776,754, the full disclosure of which is incorporated herein by reference. As illustrated in FIG. 1, a patient's heart 24 has been treated by deployment of an implant across a lower portion of the left ventricle 32 between septum 28 and a left wall or myocardium region 34. The implant generally includes a tensile member which extends between anchors 36 and 38.

A variety of alternative implant structures and methods have also been proposed for treatment of the heart. U.S. Pat. No. 6,059,715 is directed to a heart wall tension reduction apparatus. U.S. Pat. No. 6,162,168 also describes a heart wall tension reduction apparatus, while U.S. Pat. No. 6,125,852 describes minimally-invasive devices and methods for treatment of congestive heart failure, at least some of which involve reshaping an outer wall of the patient's heart so as to reduce the transverse dimension of the left ventricle. U.S. Pat. No. 6,616,684 describes endovascular splinting devices and methods, while U.S. Pat. No. 6,808,488 describes external stress reduction devices and methods that may create a heart wall shape change. Each of these patents is also incorporated herein by reference.

While the proposed implants may help surgically remedy the size of the ventricle as a treatment of congestive heart failure and appear to offer benefits for many patients, still further advances would be desirable. In general, it would be desirable to provide improved devices, systems, and methods for treatment of congestive heart failure. It would be particularly desirable if such devices and techniques could increase the overall therapeutic benefit for patients in which they are implanted, and/or could increase the number of patients who might benefit from these recently proposed therapies. Ideally, at least some embodiments would include structures and or methods for prophylactic use, potentially altogether avoiding some or all of the deleterious symptoms of congestive heart failure after a patient has a heart attack, but before foreseeable disease progression. It would be advantageous if these improvements could be provided without overly complicating the device implantation procedure or increasing the trauma to the patient undergoing the surgery, ideally while significantly enhancing the benefits provided by the implanted device.

BRIEF SUMMARY OF THE INVENTION

The present invention generally provides improved devices, systems, and methods for treating a diseased or at-risk heart of a patient. Embodiments of the invention may make use of structures which decrease or limit a size of a chamber of the heart, such as by deploying a tensile member to bring two walls of the heart (one of which is usually, but not necessarily the interventricular septum) into contact, thus diminishing a circumference of the chamber. In addition to limiting a dimension across the chamber, the implant may include an electrode or other structure for applying signals (often as electrical potential or voltage, current, or the like) to one or both ventricles of the heart, such as for defibrillating the heart, pacing the heart, or the like. In many embodiments, the implant may sense motion, intercavity pressure, oxygen saturation, flow, activation potentials, or other measurements of function or beating of the heart, optionally using the same electrodes and/or other sensor surface(s) of the implanted device. Exemplary embodiments of the implant may be included within a hardwired and/or wireless telemetry and control system, allowing the implant to not only treat congestive heart failure and monitor the results of the treatment, but to apply appropriate electrical stimulation based on monitored activity of the treated heart.

In a first aspect, the invention provides a method for treating a diseased or at-risk heart. The heart has a first chamber bordered by a septum and a wall. The heart has a second chamber separated from the first chamber by the septum. The method comprises deploying an implant through the septum. The implant includes a tensile member, and the tensile member is tensioned between the septum and the wall to limit a dimension of the heart. Signals are transmitted with the implant. Optionally, the signals may pace the heart. The signals can also be used for defibrillation. The signals may alternatively be used to sense beating and/or other functional measurements of the heart. Combinations of any of the three of pacing, defibrillating, and sensing may also be provided, so that the signals may comprise stimulation signals and/or monitoring signals.

The tensile member will often pull the wall toward the septum while the implant transmits the pacing signals transceptally. In many embodiments, the tensile member may be drawn into engagement with the septum. The chamber will often comprise a left ventricle of the heart, with the wall and septum engaging each other sufficiently to effectively exclude a portion of the wall and septum from the functioning left ventricle. The excluded portion will often comprise scar tissue.

The implant will often be used to facilitate biventricular pacing of the left and right ventricles. The tensile member may extend through scar tissue of the heart and a pacing lead may be included in the implant, with the pacing lead extending from the scar tissue adjacent the tensile member to a functioning, contractile tissue remote from the tensile member. In some embodiments, contractile heart tissue signals of the left and/or right ventricle may be sensed using the leads of the implant. The implant may also be used to defibrillate the left and/or right ventricle, with defibrillation voltage optionally being transmitted from (or from adjacent to) the tensile member via the scar tissue, and/or from one or more electrode surfaces separated from the tensile member.

First and second anchors may affix the tensile member to the septum and wall of the heart, thus effectively sealing the septum around signals that are transmitted transceptally. Defibrillation signals may be passed from the implant to the heart by using an electrode surface of at least one of the anchors, such as through use of an electrode surface along the anchors or the like. Where the implant extends through the wall, the second anchor may engage and apply heart defibrillation voltage to an epicardial surface of the wall. In some embodiments, a lead for pacing or sensing contractions may be deployed at a location which is separated from that of the anchors. For example, the implant may optionally help measure heart contractile signals along an epicardial surface of the wall or from the septum using such leads.

The implant will often be coupled to a processor having a first mode and a second mode. The implant in the first mode may monitor beating of the heart in response to sensed heart signals, and may transmit (wirelessly or by hardwire) output signals indicative of beating of the heart. The implant in the second mode may pace or defibrillate the heart, with the implant optionally having three modes to facilitate sensing, pacing, and defibrillation.

In another aspect, the invention provides an implant for treating a heart. The heart has a first chamber bordered by a septum and a wall and a second chamber separated from the first chamber by the septum. The implant comprises a first anchor couplable to the septum a second anchor couplable to the wall. Separation or distance between the second anchor and the first anchor can be constrained so as to limit a dimension across the first chamber of the heart. A pacing electrode surface, defibrillating electrode surface, and/or sensing surface may be provided, or some other sensor may be included. A signal transmission conductor extends between (often being just a portion of the distance between) the first anchor and the second anchor. The conductor is coupled to the surface to allow electrical heart signal transmission.

The surface will often comprise a pacing and/or sensing electrode surface. Insulation may extend along an axis between the anchors for isolating pacing and/or beat sensing signals from blood and adjacent heart tissue. A tensile member will typically couple the first anchor to the second anchor so as to limit the separation therebetween, with the insulation often covering at least a portion of the tensile member, and hence, the tensile member may also comprise the conductor. In other embodiments, a separate conductor for transmitting signals may extend along at least a portion of the tensile member with the insulation disposed therebetween. The conductor may have single or multi-channel signal transmission capabilities within the implant.

In many embodiments, the electrode surface may comprise a first electrode surface disposed along the first anchor. A second electrode surface may be disposed along the second anchor. In such embodiments, a defibrillator power source may be coupled with the electrode surface(s). The power source may comprise a battery, and may be implanted in the patient.

In some embodiments, the electrode surface may comprise a tip or surface of a pacing lead. A conductor may extend from the first anchor, the second anchor, and/or the tensile member to the pacing lead. A second pacing lead and associated conductor may also be provided, with each pacing lead optionally being disposed in an associated ventricle of the heart so as to provide biventricular pacing. Multiple leads may also be used in each ventricular.

A heartbeat signal processor may be coupled with the electrode surface, with the processor monitoring beating of the heart. Hardwired or wireless telemetry and/or control signals may be sent to or from the implant. The implant may generally have a sensing mode and another mode, with transmission of hardwired or wireless signals from the implant in the sensing mode indicating beating of the heart to an external processor. In the other mode, the implant may provide stimulation signals or potentials to the heart, such as by applying pacing or defibrillating the heart.

In another aspect, the invention provides an implant for biventricular pacing of a heart. The heart has a first chamber with scar tissue, the first chamber bordered by a septum and a wall. The heart has a second chamber separated from the first chamber by the septum. The implant comprises an elongate tensile member having an access. A first anchor is couplable with the tensile member to affix the tensile member to the septum. A second anchor is couplable with the tensile member to affix the tensile member to the wall. Tensioning of the tensile member effectively excludes at least a portion of the scar tissue from the first chamber. A first pacing electrode surface is separated from the first anchor for positioning within the chamber beyond the scar tissue. A second pacing electrode surface is separated from the second anchor for positioning within a second chamber beyond the scar tissue. A biventricular pacing signal source is coupled with the first and second electrode surfaces.

In another embodiment, the invention provides an implant for defibrillating the heart. The heart has a first chamber bordered by a septum and a wall, and a second chamber separated from the first chamber by the septum. The implant comprises an elongate tensile member having an axis. A first anchor is couplable with the tensile member to affix the tensile member to the septum. A second anchor is couplable with the tensile member to affix the tensile member to the wall so that tensioning of the tensile member limits a dimension of the first chamber. A first electrode surface is disposed along the first anchor, and a second electrode surface is disposed along the second anchor. A defibrillation signal source is coupled with the first and second electrode surfaces.

BRIEF DESCRIPTION OF THE DRAWINGS

FIGS. 4A-4E are cross-sectional views schematically illustrating methods for accessing, identifying, and penetrating tissues for deployment of the implant system of FIGS. 2 and 2A.

DETAILED DESCRIPTION OF THE INVENTION

The present invention generally provides improved devices, systems, and methods for treatment of a heart. Embodiments of the invention may be particularly beneficial for treatment of congestive heart failure and other disease conditions of the heart. The invention may find uses as a prophylactic treatment, and/or may be included as at least a portion of a therapeutic intervention.

Myocardial infarction and the resultant scar formation is often the index event in the genesis of congestive heart failure. The presence of the scar may, if left untreated, lead to a compensatory neuro-hormonal response by the remaining, non-infarcted myocardium. The systems, methods, and devices described herein may be applied to inhibit, reverse, or avoid this response altogether, often halting a destructive sequence of events which could otherwise cause the eventual failure of the remaining functional heart muscle.

Embodiments of the present invention may build on known techniques for exclusion of the scar and volume reduction of the ventricle. Unlike known techniques that are often accomplished through open surgery, including left ventricular reconstruction, ventricular restoration, the Dor procedure, and the like, the treatments described herein will often (though not necessarily always) be implemented in a minimally invasive manner. Embodiments of the invention can provide advantages similar to those (for example) of surgical reconstruction of the ventricle, resulting in improved function due to improved dynamics, and by normalizing the downward cycle initiated by the original injury and mediated by the neuro-hormonal disease progression response. In some embodiments, the implants and systems described herein may be included with other surgical therapies, such as by augmenting or replacing the implantation of an implantable defibrillator, pacemaker, valve surgery, or the like.

Advantageously, the methods, devices, and systems described herein may allow percutaneous left ventricular scar exclusion and ventricle volume reduction to be applied at any appropriate time during the course of the disease. Rather than merely awaiting foreseeable disease progression and attempting to alleviate existing cardiac dysfunction, the techniques described herein may be applied proactively to prevent some or all of the heart failure symptoms, as well as to reverse at least a portion of any existing congestive heart failure effects, to limit or halt the progression of congestive heart failure, and/or to retard or prevent congestive heart failure disease progression in the future. Some embodiments may, for appropriate patients, limit the impact of myocardial infarction scar formation before heart failure ever develops.

Figure 1:
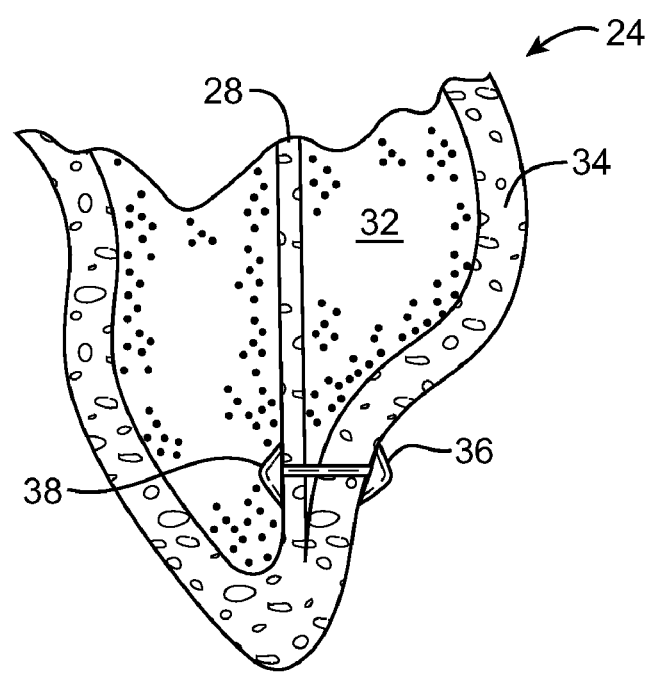
FIG. 1 is a cross-sectional view schematically illustrating a known implant and method for closing off a lower portion of a heart ventricle, as described in the background section.
Figure 2:
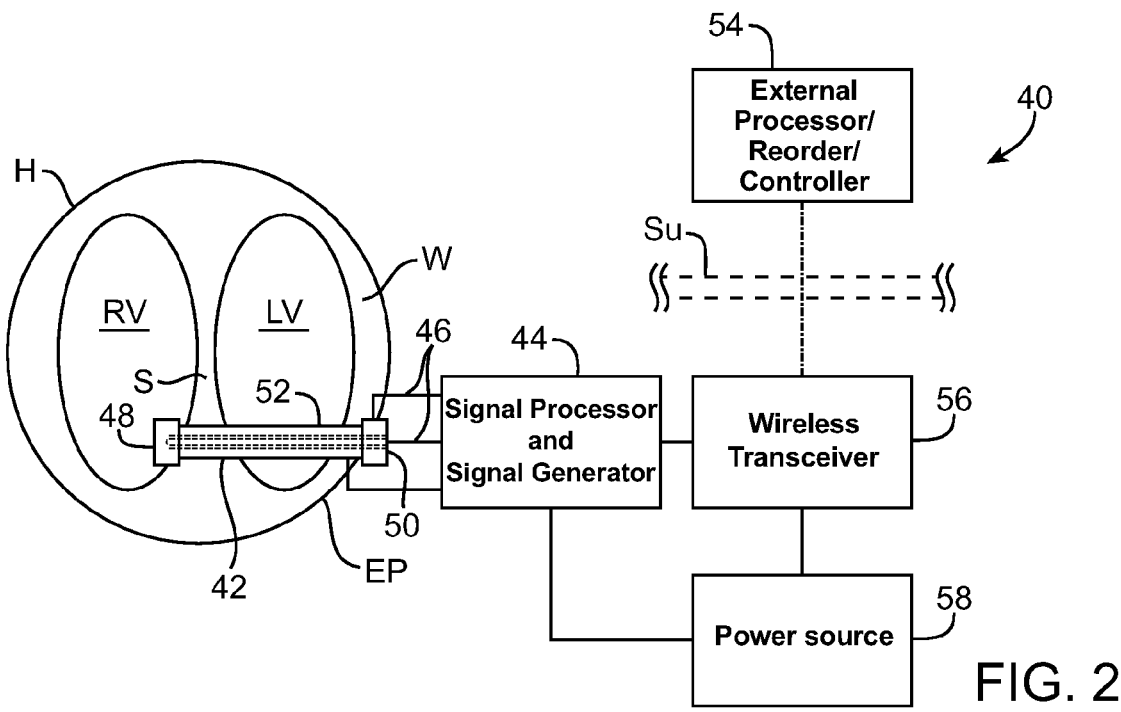
FIG. 2 schematically illustrates a system according to an embodiment of the invention, in which an implant limits a dimension of a chamber of the heart, and in which anchors of the implant are used for signal transmission, for example to defibrillate the heart when appropriate.

Referring now to the illustration of FIG. 2, an exemplary implant system 40 comprises an implant 42 and is used to treat a heart H of a patient. Implant 42 generally extends from within a right ventricle RV, through a septum S, traverses a left ventricle LV and a wall W of the left ventricle, to an epicardial surface EP.

Figure 2A:
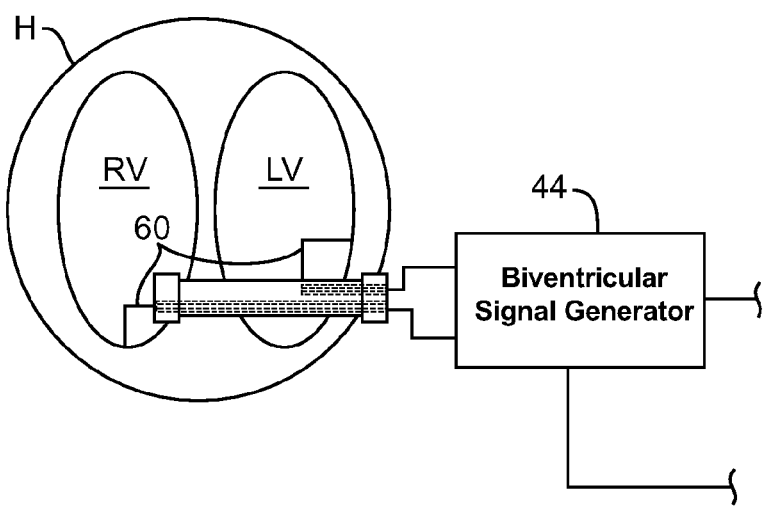
FIG. 2A is a schematic of a system related to that of FIG. 2, in which leads extend from the implant to contractile tissue to facilitate biventricular pacing and/or heart signal sensing using the implant.

Implant system 40, implant 42, and heart H are schematically illustrated in FIGS. 2 and 2A. Although the implant is shown extending through an open left ventricle, many embodiments will, when fully deployed, bring the septum S and wall W together to effectively limit the size of left ventricle LV and exclude scar tissue. Nonetheless, some alternative embodiments of the implants described herein may extend across a partially or fully open left ventricle, even when the system is fully deployed.

As illustrated in FIG. 2, implant 42 is electrically coupled with a signal processor and/or signal generator (hereinafter "processor 44") via one or more electrical conductors 46. Implant 42 generally comprises a septal anchor 48, a wall anchor 50, and a tension member 52 therebetween, and any one or more of these components may have active electrode surfaces which are electrically coupled to signal processor and generator 44 by associated conductors 46. As the tensile member 52 and anchors 48, 50 may engage scar tissue, such anchor-mounted electrodes may be suitable for defibrillation of the heart or the like. Pacing and sensing of the heart contractions may be facilitated by use of an electrode surface separated from anchors 48, 50 to engage adjacent contractile tissues, often through the use of separate lead structures as described below. Electrograms measured using electrodes engaging contractile tissues may be of greater diagnostic value than those recorded via scar tissue, although alternative embodiments may make use of such scar-engaging electrodes to obtain heart cycle data.

Processor 44 may be partially or fully implanted under a skin SK of the patient. In embodiments having at least a portion of the signal processing and/or generating performed outside of the skin SK, communications between implant 42 and an external processor 54 (or between the implant and an implanted processor) may be effected using a wireless transceiver 56. Such communications may also allow external recording and/or monitoring of heart activity or implant performance, external commands to be transmitted to the implant, or the like. A power source 58 such as a battery or the like may be implanted below the skin, with the power source optionally being chargeable through the skin using known inductive medical device battery charging structures. In some embodiments, most or all of the data processing may be handled by the external processor 54. Some embodiment may also make use of wires extending through the skin SK to transmit signals to or from the heart H via implant 42, and/or to supply power to the implant.

Exemplary embodiments of anchors 48, 50 will selectively couple tissue-engaging electrodes of implant 42 with processor 44. Other portions of implant 42, including portions exposed to blood within the heart, organs surrounding the heart, and the like may be electrically isolated from signals transmitted to or from the heart by electrical insulation materials and/or a housing. Separate tissue-engaging regions of implant 42 may be separately coupled to processor 44 for measuring heart contractions at different locations in the heart, for transmitting separate stimulation potentials to different heart tissues, for applying bipolar potentials across the implant, and/or the like.

Processor 44 may comprise digital and/or analog circuitry, often comprising an integrated digital signal processing circuit programmable with machine-readable computer programming instructions or code. The code will typically be embodied in a tangible media of the processor, using a non-volatile memory, a random access memory, or the like. Suitable processing structures that may be modified for use as processor 44 in system 40 include many of those processors now used in implantable cardiac stimulation systems such as implantable cardioverter-defibrillators and the like. Wireless transmission systems included in system 40 may be adapted or modified from structures included in these same known systems, or wireless transmission structures included in neural stimulation devices, implantable insulin pumps, glucose monitoring devices, and in a variety of other implantable structures. Other embodiments may rely entirely on internal signal processing and generation in some or all modes of operation, or the data processing and energy storage may be fully self-contained within the implant. A wide variety of internal and/or external centralized or distributed data processing techniques might be implemented. Power sources developed for these and other devices may be used as power source 58, or a proprietary power source may be included.

Wireless energy and/or data transmission to or from the implant 42 may reduce the complexity and trauma of system deployment, and a variety of wireless energy transmission arrangements for the components of system 40 may be employed. For example, a battery within implant 42 may provide sufficient energy to sense local electrograms, to pace the heart, and the like. In some embodiments, electromagnetic energy for heart beat monitoring and pacing may be transmitted from outside the patient body and to the implant 42 from an external power source. Suitable techniques for such energy transmission may include those (or be modified from those) developed by Advanced Bionics Corporation of Sylmar, Calif. The significantly greater energies associated with defibrillation of the heart will often be provided by a battery implanted outside the heart tissue and electrically coupled to implant 42 by an electrical conductor.

Referring now to FIGS. 2 and 2A, a variety of different signals may be sent between heart H and processor 44 via implant 42. In many embodiments, surfaces of the implant may comprise electrode surfaces and may be used to sense cardiac contraction signals, the sensed signals typically comprising electrograms. Electrode surfaces of implant 42 may also be used to transmit stimulation signals and/or voltages from processor 44 to the heart, such as for defibrillation, pacing, and the like. Where implant 42 is used to limit a size of a left ventricle and exclude scar tissue, at least some of the tissues engaged by the implant structure may comprise or form non-contractile scar tissue. Defibrillation potentials may be applied through such scar tissue, so that surfaces of anchors 48, 50 and elongate member 52 may be suitable for use as electrode surfaces. In contrast, for transmission of pacing signals or voltages from processor 44 to tissues of the heart H and for cardiogram sensing, it will often be advantageous to include conductors or leads 60 extending beyond the scar tissue to engage contractile tissue of the heart. While shown schematically in FIG. 2A as engaging endocardial tissues, pacing signals or voltages may optionally be applied to the myocardium, along an epicardial surface, or the like.

The cardiac monitoring and treatment functions and structures of processor 44 can make use of known technologies, particularly those developed for existing implanted heart monitoring and treatment devices. In some embodiments, implant 42 (and any associated leads thereof) might be electrically coupled to one or more lead ports of an implantable heart monitoring and stimulation device such as the CONTAK RENEWAL® cardiac resynchronization therapy defibrillator (CRT-D), available as Model H135 from Guidant (now owned and managed by Boston Scientific Corp. of Massachusetts). This device provides cardiac resynchronization therapy for the treatment of heart failure by providing electrical stimulation to the right and left ventricles to synchronize ventricular contractions, and provides ventricular tachyarrhythmia therapy to treat ventricular tachycardia (VT) and ventricular fibrillation (VF), rhythms that are associated with sudden cardiac death (SCD). The CONTAK RENEWAL® CRT-D features independent left ventricle and right ventrical channels that are independently programmable, and that may be coupled to left ventricle and right ventricle leads of implant 42. Such devices also allow monitoring of the heart rate, activity, and the like, and may also generate defibrillation signals or voltages (with defibrillation voltages optionally being transmitted through anchor surface electrodes). Processor 44 might alternatively comprise an InSync® ICD (implantable cardioverter defibrillator) from Medtronic, which was designed to combine defibrillation and resynchronization therapy, and to monitor the electrical conduction system of the heart and deliver lifesaving therapy for ventricular arrhythmias and defibrillation impulses if necessary. Still further alternatives include the Frontier® CRT Biventricular Stimulation Device (from St. Jude Medical, Inc., of St. Paul, Minn.) a multiple port, multi-chamber device for stimulating the heart in a biventricular or left-ventricular fashion to promote resynchronization and improved hemodynamic performance.

Patients who are candidates for left ventricular reconstruction may be at much higher risk of sudden cardiac death due to ventricular fibrillation. In such patients, implantation of system 40 having the capabilities of an ICD may increase life expectancy. Such benefits may come largely or primarily from automatically shocking the patient into a regular rhythm soon after ventricular fibrillation or a very fast ventricular tachycardia is sensed by processor 44. One or more implants 42 may be used to treat the left ventricle of a single patient, and their one or more anchor(s) 50 on the anterior free wall of the left ventricle could be used as an effective shocking electrode (with multiple anchors 50 optionally being connected together to serve as a single electrode). These anchors may be located on the anterior part of the free wall of the left ventricle apical to all viable muscle in the ventricle. A defibrillating shock might be (for example) delivered between such a free wall anchor(s)/defibrillating electrode(s) and a defibrillating electrode placed in the right atrium, particularly a right atrium electrode located in the posterior aspect of the heart. Any of a wide variety of commercially available defibrillating electrodes structures might be coupled to the right atrium, with the lead coupling the right atrium electrode optionally (though not necessarily) being integrated into implant 42, such as by traversing the septum using a lead extending along or through the tension member. This arrangement may be capable of providing high voltage gradients to most or all ventricular muscle in the heart. These two general electrode positions will be well positioned in space to provide an effective defibrillation pulse using defibrillation shock energies, including those commonly delivered from commercially available ICDs.

Left ventricular reconstruction using the techniques described herein may also improve heart function in patients that suffer a large anterior/apical infarct due to left anterior descending artery ("LAD") occlusion or severe narrowing, often by changing the physical dimensions of the left ventricle to enable the surviving heart muscle to work more effectively. Improvement in heart function may also be achieved by reducing the amount of non-synchronous contraction of the muscles in the left ventricle. The infarct may interrupt the normal activation pathways for the heart, resulting in contractions in different parts of the left ventricle being somewhat out of sync with each other. This lack of synchronicity both increases the work of the heart and decreases its ability to pump blood. Pacing the left ventricle at two or more sites using the systems and methods described herein may result in a more synchronous contraction that improves the pump efficiency of the heart.

Figure 3A:
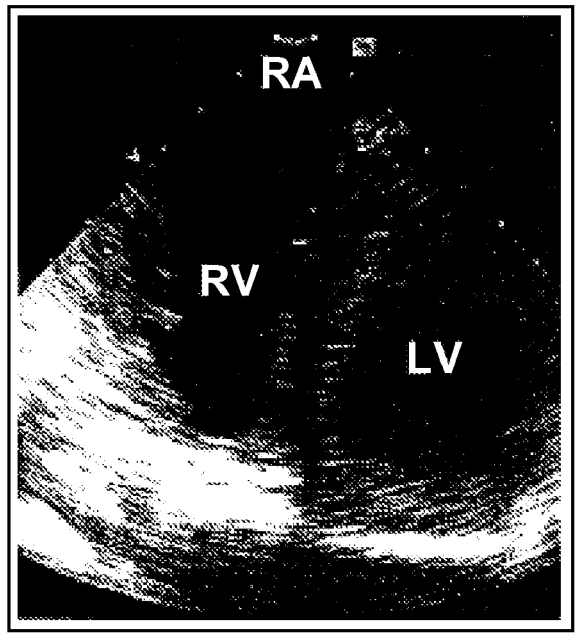
FIGS. 3A and 3B illustrate examples of images of the heart and/or devices disposed therein that may be used to direct deployment of embodiments of the invention.
Figure 3B:
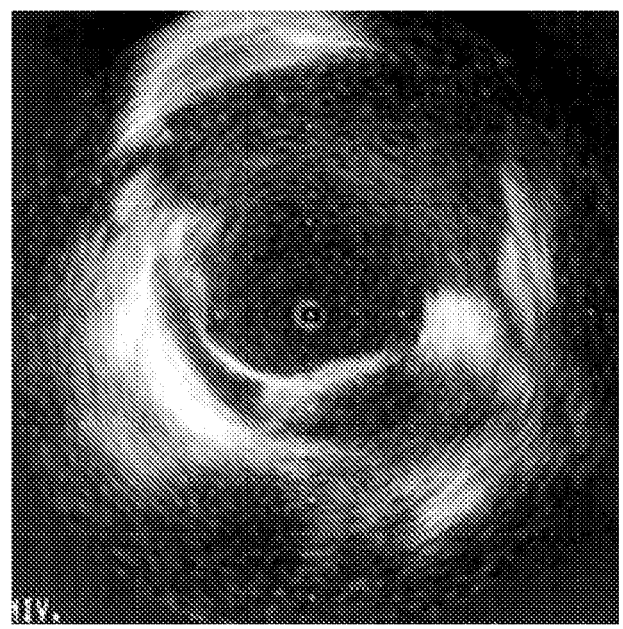

Referring now to FIGS. 3A and 3B, deployment of the implants described herein and implementation of the therapies will benefit from accurate and reliable identification of the margins separating the scar and viable, contractile myocardium. Such identification can be accomplished, for example, using pre-operative imaging, catheter-sensed activation potentials, pacing thresholds, ultrasonic imaging characteristics, biomarkers, or a variety of other tissue imaging and/or characterization methodologies. In general, it will be beneficial to provide information to the physician deploying the system to allow accurate characterization of selected locations as substantially comprising scar tissue or substantially comprising a viable contractile tissue. Additionally, the geometry of the chambers of the heart, and particularly the left ventricular chamber, should be clearly imaged to facilitate the desired reduction in size of the left ventricular chamber. This imaging may be accomplished by one imaging modality or by a combination of different imaging modalities. Exemplary imaging modalities which may be employed for identification of the heart geometry and/or tissue characterization include: echocardiography (including intracardiac echocardiography ("ICE") and/or extra-cardiac echocardiography (such as transesophageal echocardiography and/or transthoracic echocardiography ("TTE" and "TEE", respectively) or the like), intra- or extra-vascular endoscopy, fluoroscopy, or any of a variety of alternative existing or new imaging techniques, either alone or in combination.

FIGS. 3A and 3B illustrate an example of ICE showing the geometry of the heart chambers, including a right atrium RA, a portion of the right ventricle RV, and the left ventricle LV along with some of the heart tissues bordering these chambers. FIG. 3B illustrates an intracardiac echocardiography image in which a catheter device within the ventricle can be seen.

Deployment of the structures described herein may also benefit from sensors that can be used to monitor the procedure, such sensors ideally providing a real-time assessment of the progress of the treatment and performance of the heart during deployment and/or as deployment is completed. The goal of deployment will often be to achieve a desired reduction in size of a chamber (typically the left ventricle), while avoiding overcorrection (which might otherwise induce acute diastolic dysfunction). Such functional assessment sensors may comprise pressure sensors, hemodynamic sensing systems, strain sensors, oxygen saturation sensors, biological marker detectors, and/or other sensors measuring heart function to permit a quantitative assessment of efficacy of the procedure as it is implemented.

Referring now to FIGS. 4A-4E, exemplary techniques and structures for accessing and penetrating the septum and left ventricular wall can be understood. First summarizing these steps, it will be advantageous to identify, engage, and temporarily hold the device in alignment with a desired position on the right ventricular septum, as schematically illustrated in FIG. 4A. Identification or characterization of the engaged tissue will also be advantageous. The septum will be penetrated as can be understood with reference to FIG. 4B, and the system is steered across the left ventricular chamber as illustrated in FIG. 4C. The system engages one or more target locations on the left ventricular wall as shown in FIG. 4D. The engaged tissue may be characterized and the system repositioned as needed, with the system being held in engagement with the left ventricular wall if found to be at an appropriate or designated position, with the system optionally attaching or temporarily affixing itself to the left ventricular wall. The left ventricular wall may then be perforated, penetrated, or otherwise transcended as illustrated in FIG. 4E.

In more detail, referring now to FIG. 4A, an access and deployment system 70 includes a catheter 72 and a penetrating/sensing perforation device 74. In some embodiments, separate devices may be used for penetrating the heart tissues and characterizing the tissues. Here, catheter 72 accesses the right ventricle RV in a conventional manner, typically by advancing the catheter over a coronary access guidewire. A distal end of catheter 72 is aligned with a candidate location along the right ventricular surface of the septum S by a combination of axial rotation of the catheter and distal/proximal positioning of the catheter, as shown by the arrows. Positioning of the catheter is directed with reference to imaging (as described above) and when the end of the catheter is aligned with the candidate location a perforation device 74 is advanced distally so that a distal end of the perforation device contacts the septum S.

Perforation device 74 may characterize or verify that the candidate location is appropriate, for example, by determining a pacing threshold at the candidate site. Scar tissue ST may have a pacing threshold which differs sufficiently from a viable tissue VT to allow the physician to verify that the candidate site comprises scar tissue and/or is otherwise suitable. If the candidate site is not suitable, the perforation device 74 may be withdrawn proximally to disengage the perforation device from the septum S, and the catheter may be repositioned as described above to a new candidate site.

Catheter 72 may comprise a commercially available steerable sheath or introducer. Deflection of catheter 72 may be effected using one or more pull wires extending axially within the catheter body. Suitable introducers include devices that can be introduced transcutaneously into a vein or artery. Suitable steerable sheaths may generally comprise a tubular catheter body with an open working lumen. The open lumen can be used as a conduit for passing another catheter into the patient body, or for introducing another device (such as a pacing lead) into the patient body. Exemplary steerable sheaths for use in system 70 may include those commercially available from the Diag division of the St. Jude Corporation. Preferably, the working lumen of catheter 72 will be in a range from about 5 F-11 F.

Regarding perforating device 74, one embodiment would comprise a deflectable or steerable catheter body (ideally comprising a 2 F-3 F catheter) with a metallic bullet-shaped electrode at its distal end. The distal electrode is connected to a signal wire that terminates in a connector outside the body. Electrogram amplitudes recorded from the distal electrode can be used to help determine if the distal tip is located over scar tissue or over viable tissue. Efficacy in characterization of engaged heart tissues (between scar tissue and viable heart tissue) may be enhanced by recording the differential signal between the tip electrode and a band electrode located less than 1 cm from the distal electrode.

Pacing from the distal tip can be employed to help avoid perforation through viable myocardium. For most patients, such a perforation site would be counter-indicated. If the heart can be paced from the tip using a 10V amplitude pacing pulse, then viable myocardium will generally be disposed within about 5 mm of the tip. When the proper penetration site has been identified, then the distal tip is electrically coupled to an electrosurgical power source unit, and penetration is enabled by applying power to the tip in cut mode. At proper power settings, this perforation method can allow a clean perforation channel to be created without the tearing that can otherwise occur with physical perforation of the septum or free wall.

Once an appropriate site has been identified and verified, the system is held in alignment with the candidate site, and may optionally be affixed temporarily at the verified site. Perforation device 74 is advanced distally into and through septum S as illustrated in FIGS. 4B and 4C. In some embodiments, perforation device 74 may have a sharpened distal tip, a rotatable helical or screw structure, or other mechanical attributes to facilitate penetration into and perforation through the myocardium. Alternative energy delivery elements (such as a variety of electrosurgical energy units, laser energy, or the like) may also be provided. In some embodiments, system 70 may employ components similar to or modified from known septum traversing systems used for accessing the left ventricle.

As can be understood with reference to FIGS. 4C and 4D, once perforation device 74 has penetrated through the septum S, manipulation of the catheter 72 under the guidance of the imaging system allows the perforation device to be steered across the left ventricle LV and into engagement with a target location along the wall of the left ventricle. The tissue at this target location may be characterized using a sensor of perforation device 74, pacing of the engaged tissue, or the like, and the end of the perforation device repositioned as needed. The preferred location for deployment of the implant may be along or adjacent to scar tissue ST. In some embodiments, system 70 may be used for positioning of a lead at a location separated from the axis of the implant tensioning member. System 70 also allows for epicardial lead placement by advancing the perforation device 74 endocardially through septum S and the myocardium of the left ventricular wall W until it is located on the epicardial surface of the heart. The perforation device 74 and/or lead may be at least temporarily fixed at that location and tested for proper pacing effect, as can be understood with reference to FIGS. 4E and 5B.

The access and deployment system 70 described above with reference to FIGS. 4A-4E may be supplemented with or replaced by a number of differing system components. For example, as can be understood with reference to FIG. 5A, a balloon catheter 80 or other sealing structure may be used, optionally being advanced within catheter 72 and/or over perforation device 74. The balloon of balloon catheter 80 may be positioned within the myocardium of septum S or the left ventricular free-wall W to anchor the deployment system temporarily to the heart tissue and control blood loss, particularly blood loss through the left ventricular wall into the extra-cardiac space. In some embodiments, two separate balloons may be used to seal both the septum and the left ventricular wall. Balloons may also be used with or as anchors of the implant device.

Still further alternative structures may be employed, perforation device 74 may have any of a variety of sensors, including pressure sensors and the like. System 70 will often comprise high contrast structures to enhance imaging, such as by including materials having high radio-opacity, echo-density, or the like. As noted above, perforation device 74 may have or be used with a cutting, drilling, or other mechanism to help in tissue penetration. Still further alternative structures may be used for steering and positioning of the deployment system and perforation device. For example, rather than manually manipulating or steering catheter 72 to position and orient the implant, the deployment system may employ robotic surgical techniques such as those now being developed and/or commercialized for manipulation of catheters. Magnetic steering of the catheter end may also be employed, and any of a wide variety of mechanical steerable or preformed catheter structures could be employed. Some or all of the components may access the left and/or right ventricular chambers using an epicardial approach, rather than the endovascular approach described above. A combination of an extracardiac and intracardiac approach may also be employed, with the components of the implant being introduced in any of a wide variety of techniques. In some embodiments, implant 42 and/or other components of the system may be deployed in an open surgical procedure. Directly accessing at least the epicardial surface of the heart may significantly facilitate positioning and deployment of implant 42, particularly for development of implant system components and techniques, including those which may later be deployed in a minimally invasive manner.

Figure 5B:
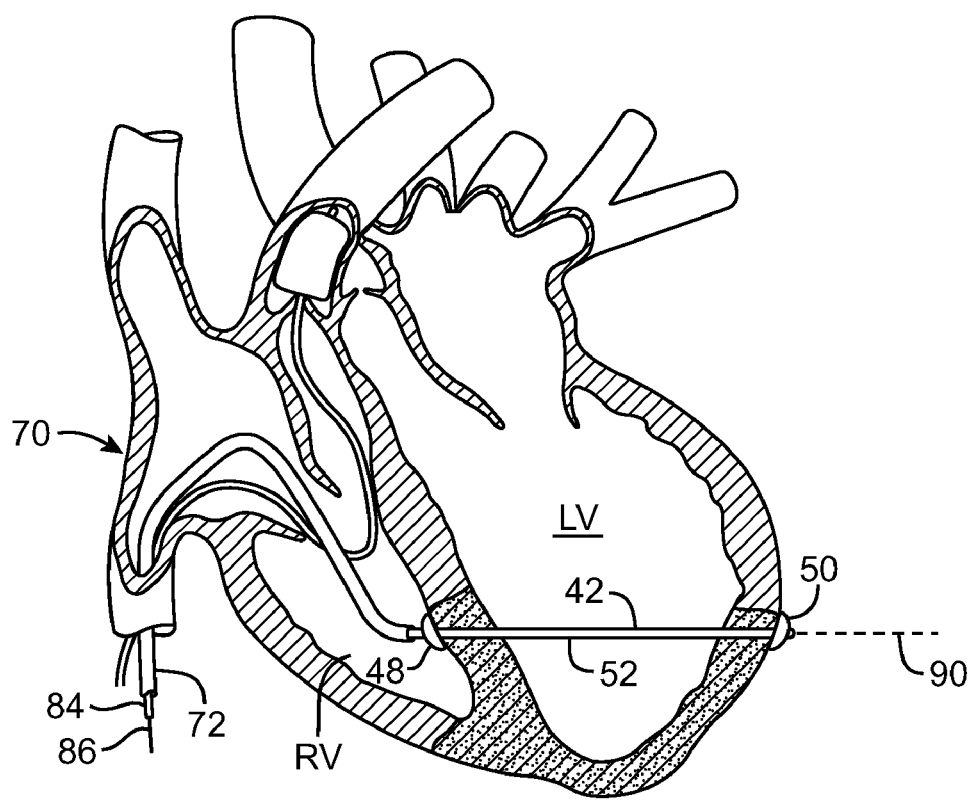
FIGS. 5A and 5B are cross-sectional views schematically illustrating initial deployment of an implant of the system of FIGS. 2A and 2B, with the implant initially being deployed in an elongate configuration.
Figure 6A:
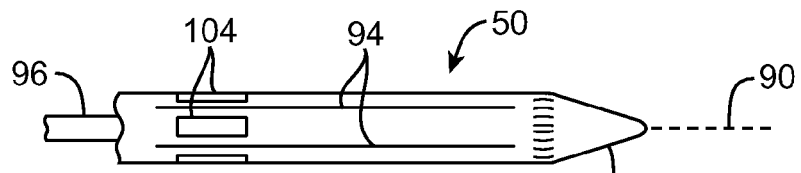
FIGS. 6A-6D illustrate deployment of an anchor for use in the implant of FIG. 5B.

Referring now to FIGS. 5B and 6A-6C, implant 42 is deployed through catheter 72 of deployment system 70, with the implant initially being deployed in an elongate configuration extending across left ventricle LV. Anchors 48, 50 of implant 42 advance distally through a lumen of catheter 72 while the anchor is in a small profile configuration, as illustrated in FIG. 6A. Anchor 50 expands from the small profile configuration to a large profile configuration, which may be effected by altering a distance between a distal end 82 and a shaft of tension member 52 using elongate bodies 84, 86 detachably coupled to the distal end 82 and tension member 52, respectively.

In general, anchors 48, 50 will be deployable through, over, or adjacent to the myocardium tissue penetrating components of deployment system 70. The anchors will attach to or otherwise engage the wall, usually by expanding or inflating into a cross section larger than that of the penetration through the heart tissue. A wide variety of anchor structures may be employed, including structures that form a disk-shaped surface or lateral extensions from an axis 90 of implant 42. As can be understood with reference to FIG. 6D, an inflatable bladder 92 or balloon of appropriate shape may be used alone or in combination with other anchoring structures. If an inflatable bladder or balloon is used, it may be filled with a substance which is initially introduced as a liquid, but which reversibly or irreversibly solidifies. Suitable fill materials may, for example, comprise liquid silicone rubber, which can polymerize at any of a variety of alternative desired rates depending on the chemistry of the material used. Optionally, the material may solidify over more than one hour, optionally over many hours or even days at body temperatures. During a procedure, such an injected liquid could be removed if desired, but the material would eventually solidify. Biological adhesives could also be delivered as fluid to fill a balloon, though cure times are relatively shorter for such materials. Such materials would irreversibly solidify.

The septal and left ventricular wall anchors 48, 50 may be identical or similar in structure, or may differ to reflect the differences between the epicardial and endocardial surfaces they engage. Fixation to the wall and septum will generally be sufficient to support the tension of tensile member 52, which will generally be capable of approximating the wall and septum, typically maintaining proximity or engagement between these structures during beating of the heart. Anchors 48, 50 and tensile member 52 will often comprise high-contrast materials to facilitate imaging, such as by including materials of sufficient radio-opacity, echo density, and the like.

In some embodiments, implant 42 may be used alone or with similar or non-signal transmitting implants to effect volume reduction over a length, width, or volume of the ventricular wall. When at least a portion of the implant 42 is deployed using an epicardial approach, left ventricular anchor 50 will often be included in the components attached from outside the heart, with tensile member 52 and/or anchor 48 being attached to this epicardial component during deployment. Robotic structures may be used to position the intracardiac or extracardiac components, and/or to attach the two of them together.

Referring again to FIGS. 6A-6D, the exemplary anchor structure comprises a Nitinol™ shaped memory alloy or other flexible material formed into a tubular shaft. Axial cuts 94 may be formed along this tubular shaft, with the cuts having a desired length and being disposed near distal end 82. Anchor 50 is advanced until the most proximal margin of cuts 94 extends clear of the heart tissue. A retraction member 96 (optionally being releasable attached to the associated elongate body 86) fixed to the inside of distal end 82 is retracted proximally, expanding the walls of the tubular shaft radially into the circumferential series of arms 98. Tissue engaging surfaces 100 of arms 98 may be substantially perpendicular to axis 90 of the implant. Arms 98 may have two general components, including the portion of the arm along tissue engaging surface 100 and a slightly longer bracing portion of the arm 102 extending away from the tissue engaging surface along axis 90. The proportionate sizes of these two elements of arms 98 may be pre-determined by localized altering of the arm stiffness (effecting the placement of living hinges) or the tubing material will otherwise preferably bend so that the arms assume a desired shape. The deployed arms may have, for example, the pyramid shape shown with the tissue engaging surface 100 supported by angled portions 102 with a pyramid-like force distribution, the angled bracing portions forming a triangular relationship with the surface of the heart wall.

Member 96 may remain within the deployed anchor, axially affixing tensile member 52 relative to the end of the anchor after deployment of the implant. This can help inhibit collapse of the arms 98. In some embodiments, arms 98 may be biased to the large cross section deployed configuration, such as by appropriate treatments to a shape memory alloy or the like. In such embodiments, member 98 or some other actuation structure may restrain the anchor in a small cross section configuration, it may not remain within the deployed implant after it is expanded.

Figure 6B:
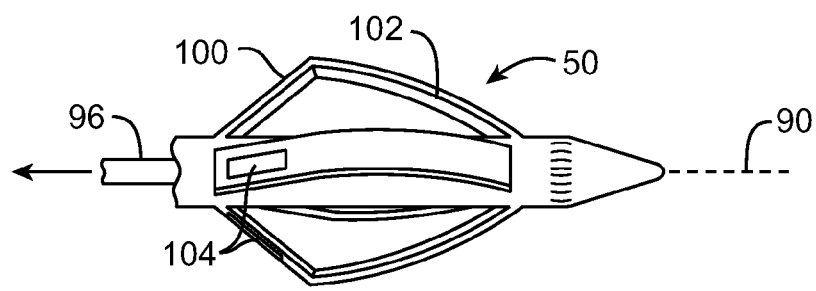
Figure 6C:
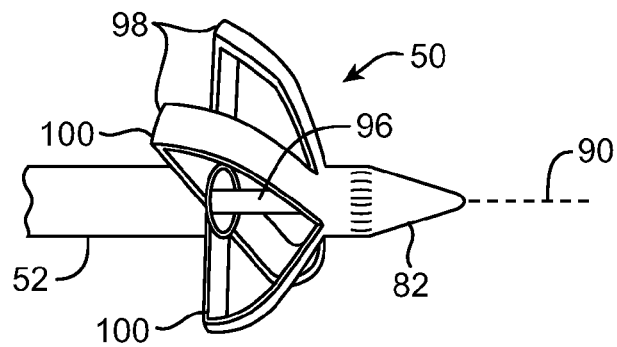
Figure 6D:
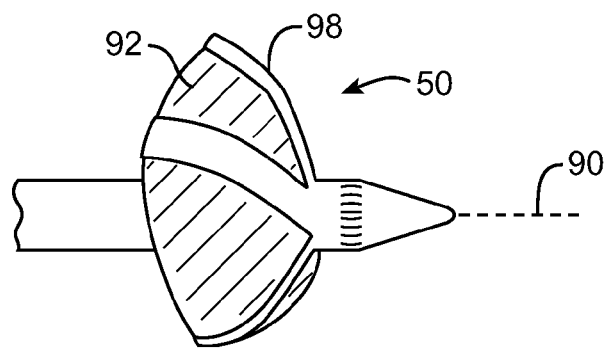

As can be understood with reference to FIG. 6D, once the anchor 50 is deployed and in position, additional support elements may be positioned or deployed through the deployment system 70. For example, a space occupying or expandable structure such as bladder 92 may be positioned or inflated within arms 98, internal support structures (optionally comprising internal pyramid-like support arms) may be deployed. The septal anchor 48 will optionally have a structure similar to anchor 50, with the proximal and distal orientations of the arm structures reversed.

While anchor 50 of FIGS. 6A-6D is shown as being integrated into a tubular shaft of elongate tensile member 52, the anchor or fixation device may alternatively comprise a separate element introduced separately over a guidewire or the like. Still further alternatives may be employed, including fixation of the heart walls by placement of magnetic materials on or within the walls, with the bodies acting as anchors and the magnetic material acting as a tensile component so as to hold the walls in apposition.

Anchors 48 and/or 50 may optionally be drug eluting. For example, bladder or balloon 92 may have a porous surface capable of eluting a substance from the film material. Alternatively, an outer surface of the balloon or the anchor structure itself may comprise a permanent or biodegradable polymer or the like, such as those that have been developed for drug eluting stents and available from a number of commercial suppliers.

Figure 5A:
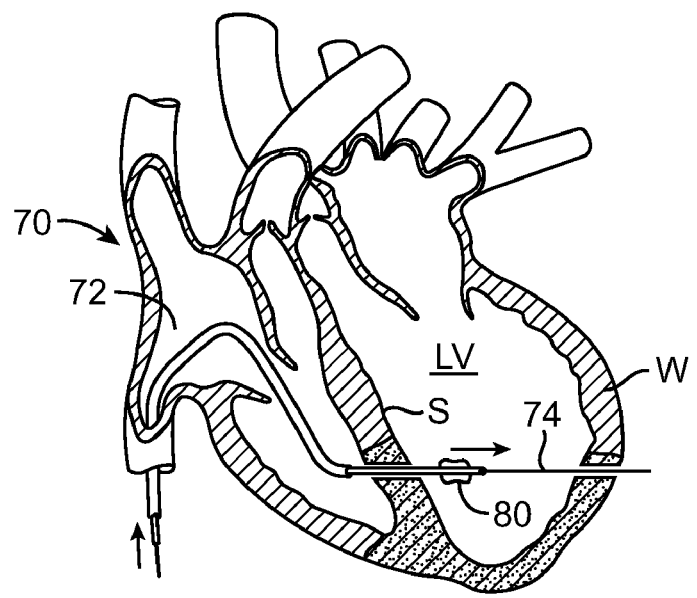
Figure 7B:
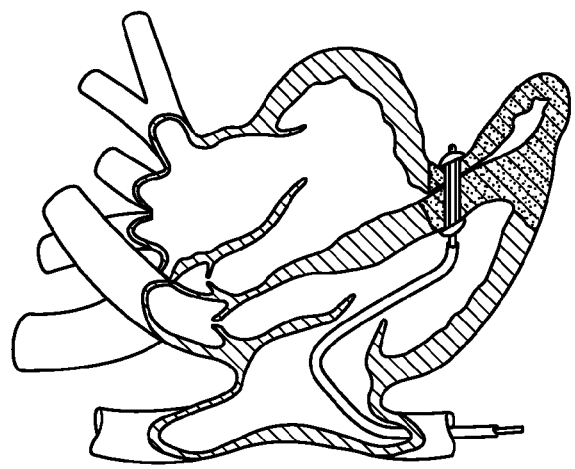
FIGS. 7A and 7B are cross-sectional views schematically illustrating shortening of the tensile member of FIG. 5B from the elongate initial configuration to a shortened deployed configuration so as to reduce a size of the left ventricle and effectively exclude at least a portion of a scar tissue from the left ventricle.
Figure 7A:
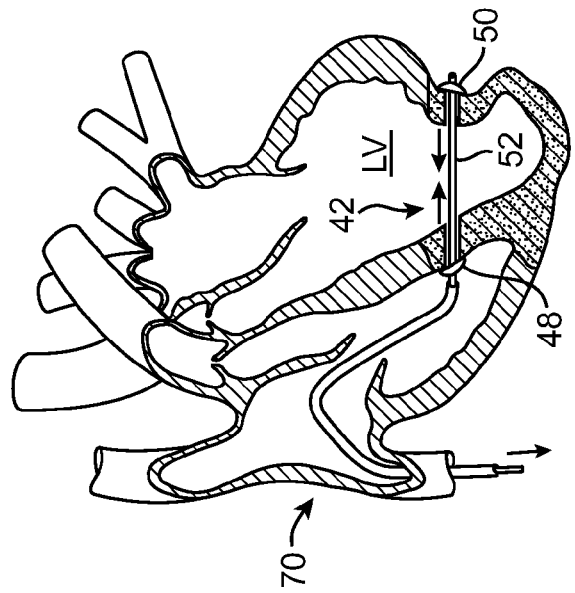

Referring now to FIGS. 5B, 7A, and 7B, after anchors 48-50 are deployed, implant 42 may be shortened from its elongate configuration with a relatively large distance between the anchors along tensile member 52 to a shortened configuration. In some embodiments, the tensile member may comprise a shaft of the tissue penetrating perforation device 74 (see FIGS. 4A-4E). In other embodiments, tensile member 52 will comprise a separate structure. In many embodiments, the tensile member and anchors will remain permanently in the heart to hold the septum and left ventricular wall in apposition. To allow shortening of the tensile member, excess length of the tensile member may be removed with the catheter 72 and other components of the delivery system, and/or some portion of the length of the tensile member may remain in the extracardiac space outside the left ventricular wall. Optionally, a ratchet mechanism may couple the septal anchor 48 to the tensile member 52, with the ratchet mechanism allowing the separation distance between the anchors to gradually decrease.

Figure 8:
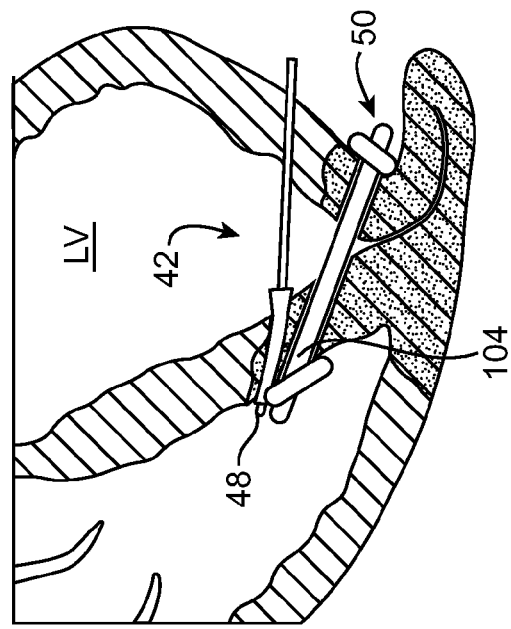
FIG. 8 is a view showing a deployed implant after removal of the delivery system.

Referring now to FIGS. 6A, 6B and 8, tissue engaging surface 100 of anchors 48, 50 may include an electrode surface 104. The electrode surface of the anchor may act as a sensing surface for detecting heart contraction, or may be used to apply stimulation voltage to the heart. For example, defibrillation potential may be applied to the heart using at least the electrode surfaces (and optionally other surfaces of the implant, including surfaces of the tensile member, other defibrillation electrodes, and the like). The defibrillation potential will preferably create a voltage gradient of at least about 5 volts/cm throughout much of the ventricles, often throughout the majority of the ventricles, and in some cases, throughout substantially all of the tissue of the ventricles. Additional leads external from implant 42 may be used to provide the desired gradients in some embodiments.

As noted above regarding FIG. 2A, implant 42 may also be used to apply pacing signals or voltages to the heart. Such pacing voltages may, however, benefit from leads extending from the implant to a pacing electrode surface sufficiently separated from the anchors and tensile member of the implant as to be disposed viable and/or contractile tissue.

Figure 9:
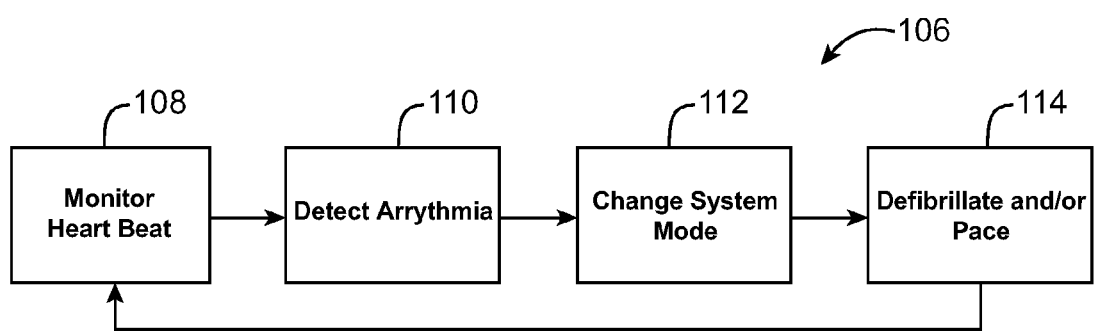
FIG. 9 is a flow chart schematically illustrating a method for treatment using the implant system of FIGS. 2 and 2A, in which a mode of the implant system changes from a monitoring mode to a stimulating mode in response to monitored heartbeat signals.

Referring now to FIGS. 8 and 9, once implant 42 is fully deployed, it may effectively exclude a portion of the septum and/or left ventricular wall (particularly a portion including or comprising scar tissue) from the functional left ventricular chamber. Additionally, the signal transmission capabilities of implant 42 may be used as a component of a rhythm management system. Other components may be coupled to implant 42 via an electrical conductor disposed in the epicardial space and extending from adjacent anchor 50, or may be incorporated into the structure of the implant. Hence, implant 42 may have embodiments in which wireless signals are sent to and from the implant without hard wiring (as described above with reference to FIG. 2), and/or implant 42 may be used as a cable/filar wire that is connected directly to other components of the implant system.

Referring now to FIG. 9, a method of use 106 of the implant systems described herein may include monitoring of the heartbeat 108 with the implant, either using electrode surface of anchors 48, 50, leads 60 separated from the anchors, or the like (see FIGS. 2 and 2A). By appropriate processing of the heartbeat signals sensed via the implant, the system may detect an arrhythmia 110 and may change the mode of the implant system 112 in response. If the processor or communication from an external controller indicates that it is appropriate to do so, the implant system may defibrillate and/or pace the heart 114. In many embodiments, the implant will limit a cross section of the left ventricle and exclude scar tissue throughout the method 106. Hence, the invention may combine left ventricular scar exclusion and volume reduction with heart signal monitoring and/or heart stimulation.

Figure 10:
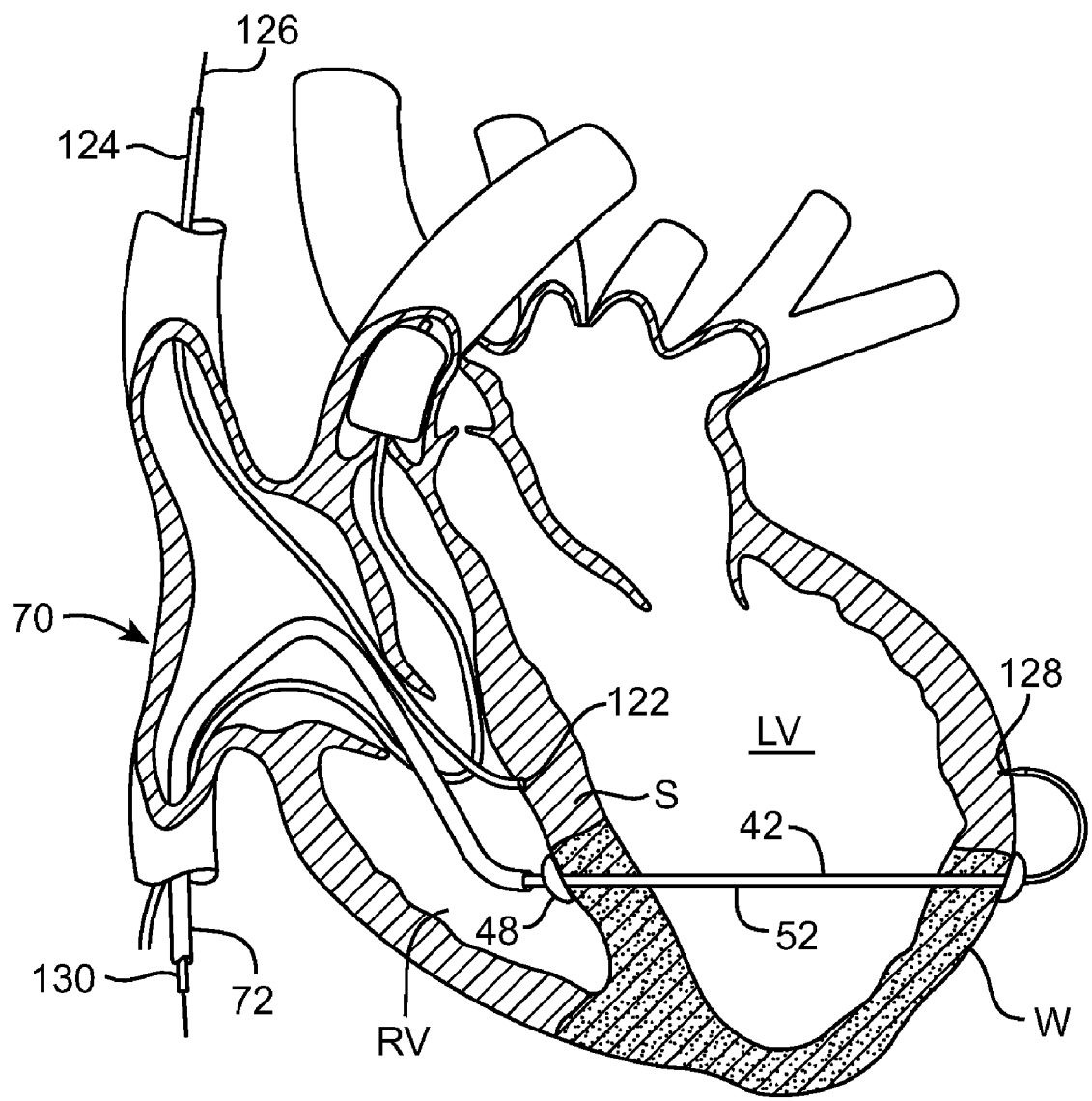
FIG. 10 is a cross-sectional view showing deployment of a pacing leads of the implant system of FIG. 2A.

FIG. 10 shows an embodiment of the implant pacing structure that can effectively improve the synchronicity of ventricular contraction. A first pacing electrode 122 is deployed from the right ventricular side of the septum using a steerable catheter 124 having a pull wire 126. Pacing electrode 122 is placed in viable tissue to provide one pacing location for the ventricle. A second pacing electrode 128 is placed in viable tissue of the free wall W of the left ventricle LV, with the second electrode being deployed through the epicardium using a resiliently deflected or steerable catheter 130. In the illustrated embodiment shown in FIG. 10, pacing lead 128 is advanced within a conduit placed though the scarred ventricular septum S and scarred infracted region of the anterior free wall W, the conduit optionally comprising a sealable lumen of implant 42 or a temporary conduit structure. For procedures done via a thoracotomy, the lead may be screwed in place using standard methods. If the procedure is to be done transcutaneously, steerable catheters 130, 124 or a deflectable sheath (similar to those described above) can be used to direct the pacing lead to the proper location on the epicardial surface and within right ventricle. The transcutaneously deployed pacing lead can be either screwed in place or (for example, when the lead has a barded tip) otherwise advanced into the target viable tissue.

When used with commercially available pacemakers already designed for multiple site stimulation, the pacemaker leads can be individually connected to the pacemaker ports on the implantable pacemaker device. Alternatively, the pacemaker leads may be connected together at a Y connection or the like, and a common lead can be connected to the pacemaker head.

Figure 11:
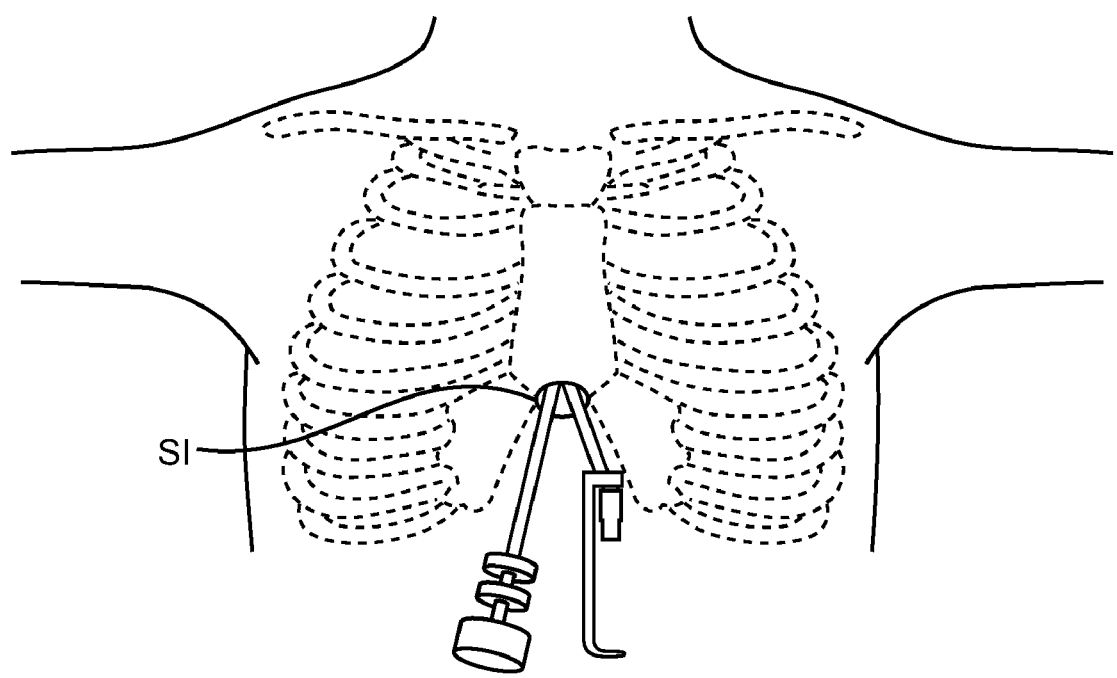
FIG. 11 schematically illustrates accessing the heart via a subxiphoid incision.
Figure 12:
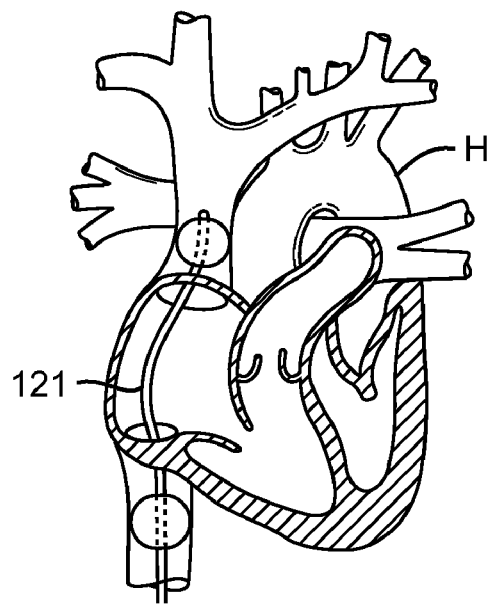
FIG. 12 illustrates a method for unloading of the heart with a double balloon catheter.

Referring now to FIG. 11, embodiments of the invention may be deployed using a subxiphoid incision SI to access the heart, and/or the ventricles of the heart. In some embodiments, additional access may be obtained through one or more intercostals space for one or more instruments. As shown in FIG. 12, a double balloon catheter 121 may optionally be used to unload the heart tissue. Double balloon catheter 121 can provide inflow occlusion to decompress the ventricles, thereby reducing the systolic pressure. This may aid in reducing the ventricular volume and/or in the exclusion of dysfunctional cardiac tissue. Double balloon catheter 121 may optionally be placed using open chest surgery. Alternatively, double balloon catheter 121 may be positioned using minimal invasive techniques, such as via a femoral or subclavian vessels or veins, and optionally being positioned percutaneously.

In some embodiments, double balloon catheter 121 may be positioned so that one balloon is in the superior vena cava and one balloon is in the inferior vena cava, thus blocking most or even essentially all blood flow from the body back to the heart. It may be easier to insert the balloon catheter either into the jugular vein or the femoral vein than it is to place using a cardiac insertion site. An alternative (and in at least some cases faster) way of off-loading the left heart is to inflate a suitably large compliant balloon in the pulmonary artery just above the pulmonic valve (proximal to the branching into the left and right pulmonary arteries). A partially inflated balloon will tend to float into the pulmonary artery from the right atrium, since blood flow carries it into that position. Hence, this may provide another method of decreasing preload on the ventricle.

Figure 13A:
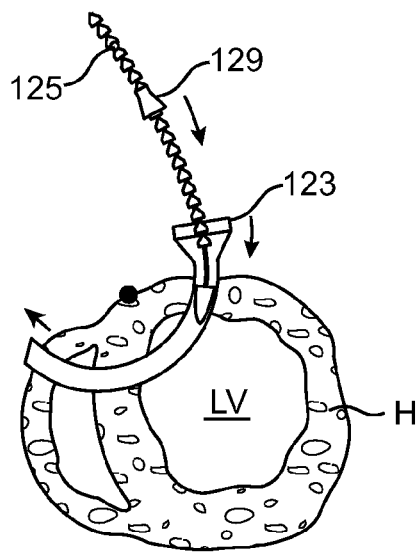
FIGS. 13A-13C schematically illustrate one variation of a transventricular implant and anchor system from a left ventricular approach.
Figure 13B:
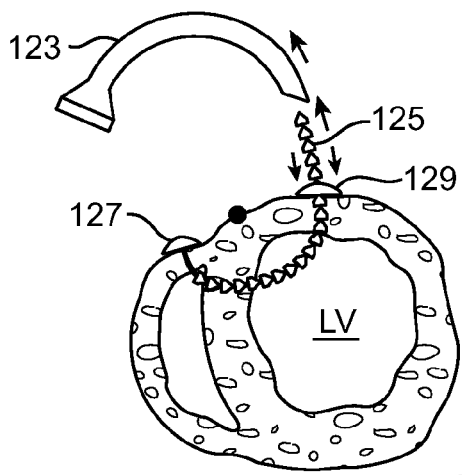
Figure 13C:
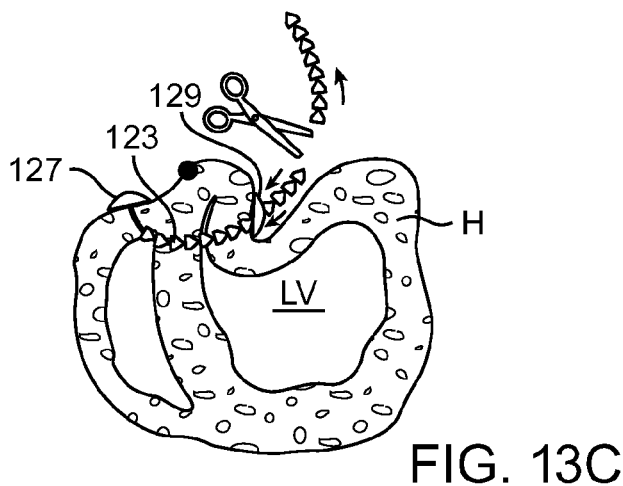

With reference to FIGS. 13A-13C, one variation of a transventricular implant and anchor system deployment from a left ventricular LV approach. A sharpened, curved tissue piercing tubular body 123 pierces the left ventricular wall, the septum, and extends back out through the right ventricular wall. This allows a ratcheted tension member 125 to be introduced through the tissues of the heart within a lumen of tubular body 123, with a first anchor 122 being attached to the tension member after insertion through the tubular body and expanded as described above or affixed after the distal end of the tension member extends free of the heart tissue. Regardless, once the tension member extends into and/or through both ventricles, the tubular body 123 can be withdrawn proximally and a second anchor 129 can be moved distally along the tension member to engage the myocardial surface of the heart, as seen in FIG. 13B. Second anchor 129 may optionally pass through the lumen of tubular body 123 and expand radially, or may be coupled to tension member 125 after the tubular body is withdrawn.

An exemplary ratcheting interface between tension member 125 and second anchor 129 may make use of a series of radial protrusions and/or detents disposed along an axis of the tension member. For example, the tension member may have slide surfaces which taper radially outwardly distally along the tension member to allow the anchor interface to slide sequentially over the slide surfaces in a distal direction, and detent surfaces which are oriented distally to engage corresponding proximally oriented surfaces of the anchor interface so as to inhibit proximal movement of the anchor relative to the tension member. Second anchor 129 may have a ratchet interface structure including (or derived from) the sealing components of a Touhy-Borst valve structure. Such an interface may resiliently deflect to pass the slide surfaces of the tension member and may grab or engage the detent surface when the tension member is pulled distally. Such a valve structure may also be increased in diameter to release the tension member if desired and/or tightened towards its smallest diameter to immovably (and optionally permanently) affix the anchor relative to the tension member. Exemplary embodiments of ratcheting tension member 123 may comprise polymers or metals, optionally comprising a polyester such as Mylar®, a thermoplastic such as Nylon™, a stainless steel, a shape memory allow such as Nitinol™, or the like.

As shown in FIG. 13C, second anchor 129 can be positioned along tension member 123 so as to effectively exclude scar tissue from the left ventricle and/or reduce a volume of the left ventricle. Some portion of tension member 123 may be disposed within the right ventricle, right ventricle scar tissue may be excluded, and/or the volume of the right ventricle may also be reduced. The tension member may be severed using a blade or the like as shown schematically, though some of the tension member may extend into the extracardiac space. In alternative embodiments using different surgical approaches (such as when using the catheter-based systems described above), at least a portion of the tension member may extend into the right ventricle or the like.

Figure 14A:
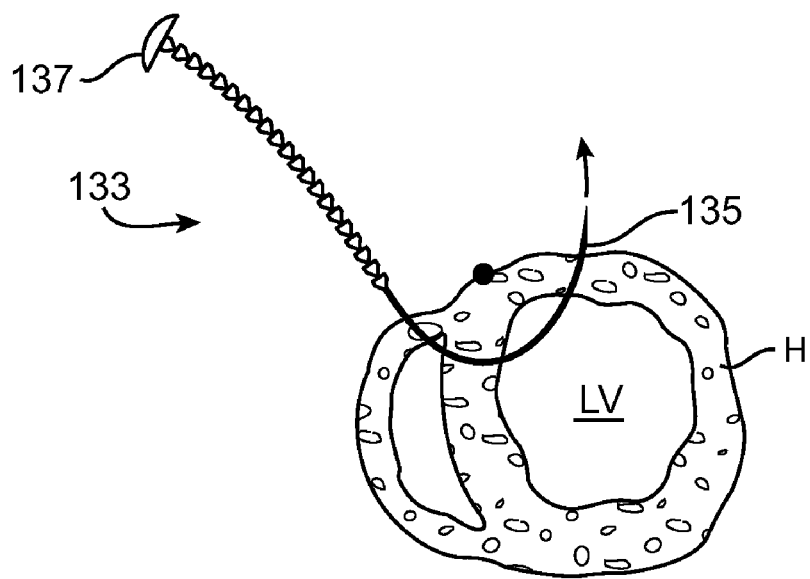
FIGS. 14A and 14B schematically illustrate another variation of a transventricular implant and anchor system from a right ventricular approach.
Figure 14B:
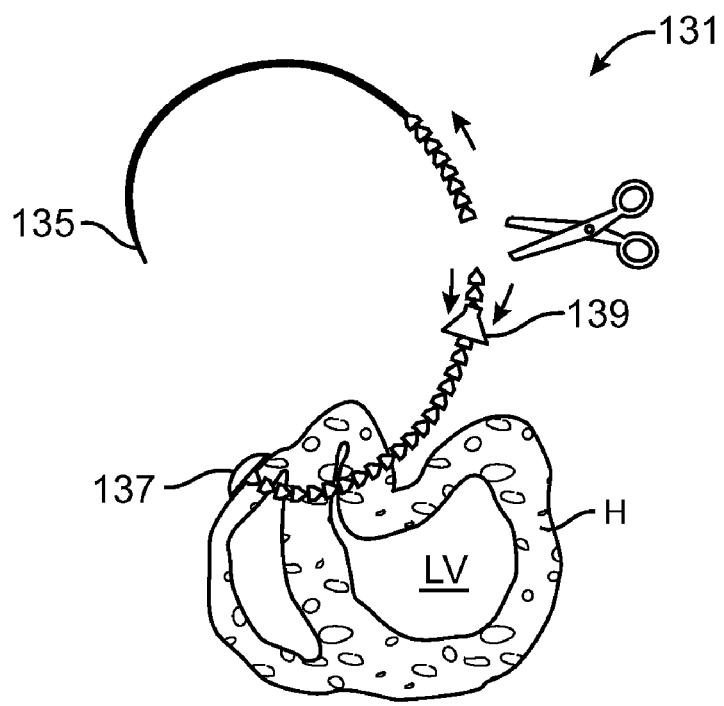
Figure 15:
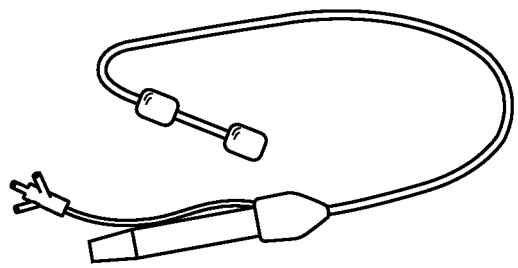
FIG. 15 illustrates a double balloon catheter for unloading of the heart in the method of FIG. 10.
Figure 16A:
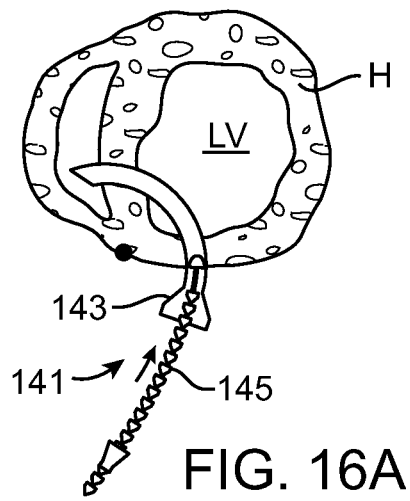
FIGS. 16A-16C schematically illustrate another variation of a transventricular implant and anchor system from a left ventricular approach.
Figure 16B:
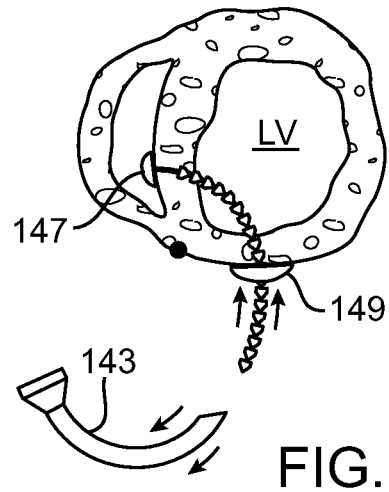
Figure 16C:
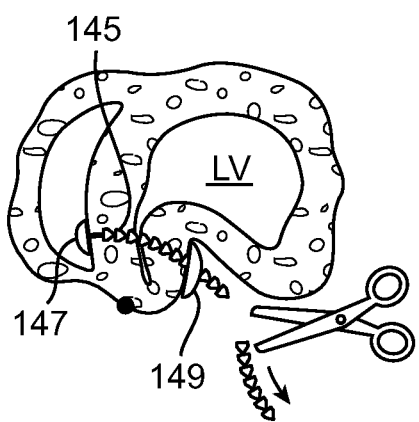

Referring now to FIGS. 14A and 14B, another alternative embodiment of an implant 131 and deployment system makes use of a transventricular approach from the right ventricle. A curved tension member 133 having a distal tissue penetrating end 135 and a proximal anchor 136 affixed thereto is introduced through the wall of the right ventricle, through the septum, across the left ventricle LV, and out through the left ventricular wall. The tension member 133 and affixed anchor 137 are advanced distally so that the anchor engages the surface of the heart, and a second anchor 139 is attached by passing distal end 135 through the anchor. Second anchor 139 is ratcheted proximally along tension member 133 to exclude scar tissue and limit a size of the left ventricle, with the distal end and at least a portion of the tension member that is distal of the positioned anchor being severed and removed from the deployed implant. FIG. 15 shows an exemplary double balloon catheter for use as described above with reference to FIGS. 11 and 12. FIGS. 16A-16C schematically illustrate another transventricular anchor system and deployment from a surgical site outside the heart similar to that of FIGS. 13A-13C, using a tubular body 143 to position a tension member 143 to which first and/or second anchors 147, 149 are ratchetably affixed.

It should be noted that the systems and methods described herein for excluding scar tissue and reducing a size of a chamber of the heart may make use of a plurality of different implants of different types and even different surgical approaches. For example, while systems may include a plurality of implants deployed from a site outside the heart (such as the embodiments shown in FIGS. 13A-13C, 14A, 14B, and 16A-16C), alternative systems may include one or more implants of one or more types deployed from outside the heart, along with one or more implants of one or more types deployed from inside the heart using a blood-vessel approach. Systems with a plurality of implants deployed from outside and/or inside the heart may benefit from any of a variety of imaging techniques so that the implant systems effectively exclude scar tissue and limit a size of one or more heart chamber.

While exemplary embodiments have been described in some detail for clarity of understanding and by way of example, a variety of modifications, adaptations, and changes will be obvious to those of skill in the art. Hence, the scope of the invention is limited solely by the appended claims.

What is claimed is:

1. A method for treating a heart, the heart having a first chamber bordered by a septum and a wall, the heart having a second chamber separated from the first chamber by the septum, the method comprising:
   deploying an implant into the septum and into the wall, the implant including a tensile member and a lead extending from adjacent the tensile member;

tensioning the tensile member between the septum and the wall to limit a dimension of the first chamber, wherein the tensile member draws tissue of the wall and the septum through which the tensile member passes into permanent engagement;

deploying the at least one lead from an epicardial surface of the heart to a contractile tissue at a different location on the epicardial surface of the heart;

transmitting signals between the implant and the heart with an electrode surface of the lead, wherein the electrode surface contacts contractile tissue, and wherein the signals are transmitted transceptally along an axis of the tensile member; and pacing, defibrillating, and/or sensing characteristics of the heart using the transmitted signals.

2. The method of claim 1, wherein the chamber comprises a left ventricle of the heart, and wherein the wall and septum engage each other sufficiently to effectively exclude a portion of the wall and septum from the functional portion of the left ventricle, scar tissue extending along the excluded portion.

3. The method of claim 1 wherein the contractile tissue is contractile tissue of the wall, and wherein the implant further comprises an additional lead extending to a contractile tissue of the septum.

4. The method of claim 1 wherein the lead is disposed within a lumen of the implant such that the lead traverses the septum and the wall through the lumen.

5. The method of claim 1, wherein the lead extends from the epicardial surface of the heart and re-enters epicardial tissue at a different location.

6. The method of claim 1, further comprising sensing contractile heart tissue signals of the left ventricle and/or right ventricle using the implant.

7. The method of claim 1, further comprising defibrillating the heart using the implant.

8. The method of claim 1, further comprising:
anchoring a first end of the tensile member to the septum with a first anchor; and
anchoring a second end of the tensile member to the wall with a second anchor.

9. The method of claim 8, wherein the anchoring of the first end of the tensile member to the septum is done so as to effectively seal the septum around transceptally transmitted signals.

10. The method of claim 8, further comprising transmitting the signals between the implant and the heart with an electrode surface of at least one of the anchors, wherein the signals comprise defibrillation signals.

11. The method of claim 10, wherein the implant extends through the wall, the second anchor engaging and applying the signals to an epicardial surface of the wall.

12. The method of claim 11, wherein the defibrillation signals are applied between the second anchor of the implant and a right atrium defibrillation lead.

13. The method of claim 8, further comprising applying the signals to the heart by pacing the heart with the lead of the implant, the lead being separated from the anchors.

14. The method of claim 8, further comprising sensing contraction using the lead of the implant, wherein the sensing comprises measuring heart contractile signals using the lead.

15. The method of claim 1, wherein the implant has a first mode and a second mode, the implant in the first mode wirelessly transmitting output signals indicating beating of the heart, the implant in the second mode pacing the heart or defibrillating the heart.

16. The method of claim 1, further comprising isolating transceptal signals from the septum with insulation extending along an axis of the tensile member.

* * * * *